United States Patent

Nédélec et al.

[11] 4,072,685
[45] * Feb. 7, 1978

[54] 3-(3',4'-DISUBSTITUTED) PHENYL PIPERIDINES

[75] Inventors: Lucien Nédélec, Le Raincy; Jacques Guillaume, Aulnay-sous-Bois; Claude Dumont, Nogent-sur-Marne, all of France

[73] Assignee: Roussel Uclaf, Paris, France

[*] Notice: The portion of the term of this patent subsequent to Sept. 6, 1994, has been disclaimed.

[21] Appl. No.: 686,090

[22] Filed: May 13, 1976

[30] Foreign Application Priority Data

May 16, 1975 France .................. 75 15382

[51] Int. Cl.² ........................................... C07D 211/22
[52] U.S. Cl. .................. 260/293.81; 260/293.82; 260/293.83; 260/293.84; 260/297 R
[58] Field of Search ............ 260/293.81, 293.82, 260/293.83, 293.84; 71/94; 424/267

[56] References Cited

FOREIGN PATENT DOCUMENTS 45-25493  1970  Japan .................. 260/293.83

OTHER PUBLICATIONS

Sugimoto et al., J. Pharm. Soc., Japan 75, 183–187, (1955).
Chemical Abstracts, vol. 50, Abstract No. 1815b, (1956), [N. Sugimoto et al., J. Pharm. Soc. Japan, vol. 75, pp. 183–187, (1955)].

Primary Examiner—Henry R. Jiles
Assistant Examiner—Richard A. Schwartz
Attorney, Agent, or Firm—Hammond & Littell

[57] ABSTRACT

Novel phenyl piperidines of the formula

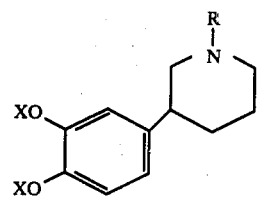

wherein X is selected from the group consisting of hydrogen and acyl of an aliphatic carboxylic acid of 2 to 6 carbon atoms and R is selected from the group consisting of alkyl of 1 to 5 carbon atoms, alkenyl of 2 to 5 carbon atoms and phenyl alkyl of 1 to 3 alkyl carbon atoms and their non-toxic, pharmaceutically acceptable acid addition salts having dopaminergic properties and certain of the compounds possess hypotensive properties.

18 Claims, No Drawings

3-(3',4'-DISUBSTITUTED) PHENYL PIPERIDINES

STATE OF THE ART

J. Pharm. Soc. Japan, Vol. 75 (1955), p. 183-187 describes N-methyl-dimethoxyphenyl-piperidine as an intermediate to prepare compounds having analgesic properties.

OBJECTS OF THE INVENTION

It is an object of the invention to provide the novel phenyl piperidines of formula I and their non-toxic, pharmaceutically acceptable acid addition salts and processes for their preparation as well as novel intermediates.

It is another object of the invention to provide novel dopaminergic compositions and to a method of treating neurological syndromes of extrapyramidal origin.

It is a further object of the invention to provide novel hypotensive compositions and a novel process for inducing hypotensive activity in warm-blooded animals.

These and other objects and advantages of the invention will become obvious from the following detailed description.

THE INVENTION

The novel compounds of the invention are selected from the group consisting of phenyl piperidines of the formula

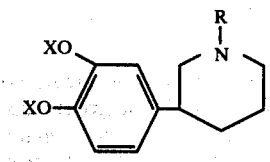   I wherein X is selected from the group consisting of hydrogen and an acyl of aliphatic carboxylic acid of 2 to 6 carbon atoms and R is selected from the group consisting of alkyl of 1 to 5 carbon atoms, alkenyl of 2 to 5 carbon atoms and phenylalkyl of 1 to 3 alkyl carbons atoms and their non-toxic, pharmaceutically acceptable acid addition salts.

Examples of X are hydrogen and acyl of alkanoic acids of 2 to 6 carbon atoms such as acetic acid, propionic acid, n-butyric acid, isobutyric acid, n-valeric acid and pivalic acid.

The acid addition salts may be derived from organic acids such as acetic acid, formic acid, benzoic acid, maleic acid, fumaric acid, succinic acid, tartaric acid, citric acid, oxalic acid, glyoxylic acid, asparatic acid; alkanesulfonic acids such as methane sulfonic acid; aryl sulfonic acids such as benzene sulfonic acid; and mineral acids such as hydrochloric acid, hydrobromic acid, hydroiodic acid, nitric acid, sulfuric acid or phosphoric acid.

Examples of R are alkyl such as methyl, ethyl, propyl, isopropyl, butyl and pentyl; alkenyl such as allyl or vinyl; and phenyl alkyl such as benzyl, phenethyl and 2-phenyl propyl. Among the preferred compounds of formula I, R is methyl, ethyl, propyl, isopropyl, allyl, benzyl and phenethyl. More preferred are those where R is the above preferred group and X is hydrogen or acetyl or pivaloyl.

The process of the invention for the preparation of the compounds of formula I comprises reacting a compound of the formula

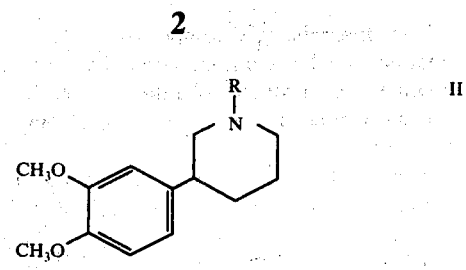   II wherein R has the above definition with hydrobromicacid to obtain the corresponding dihydroxyphenyl compound in the form of its hydrobromide salt which may be isolated per se or made, alkaline to recover the free base and salified if desired or reacting the dihydroxyphenyl compound with an acid anhydride of the formula $(X')_2-O$ wherein $X'$ is acyl of an aliphatic carboxylic acid of 2 to 6 carbon atoms or with an acid halide of the formula $X'$-Hal where $X'$ has the above definition and Hal is bromine or chlorine in the presence of a strong acid to obtain the corresponding diacyloxy phenyl compound which may be in the form of its acid addition salt or made alkaline to recover the free base.

The preferred reaction conditions for the reaction with hydrobromic acid is to reflux the product of formula II in concentrated hydrobromic acid for 1 to 5 hours and the reaction of the corresponding dihydroxyphenyl product in the form of its hydrobromine salt with an acid anhydride is effected at room temperature in the presence of an alkali metal acetate such as sodium acetate. The reaction with the acid halide is preferably effected with the acyl bromide in the presence of a strong acid such as trifluoroacetic acid. The hydrobromide salts may be converted to the free base by action with a weak base such as an alkali metal bicarbonate.

The acid addition salts of the compounds of formula I may be prepared by reaction of the free base with a stiochiometric amount of the desired acid and preferably the salts are obtained without isolating the free bases.

The novel dopaminergic compositionsof the invention are comprised of an effective amount of at least one compound of formula I and/or their non-toxic, pharmaceutically acceptable acid addition salts and an inert pharmaceutical carrier. The compositions may be in the form of tablets, dragees, gelules, capsules, granules, suppositories or injectable solutions or suspensions prepared in the usual manner.

The inert pharmaceutical carrier may be the usual excipients such as talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, dispersions or emulsifiers.

Among the preferred products for the compositions are N-methyl-3-(3',4'-dihydroxyphenyl)-piperidine hydrobromide, N-methyl-3-(3',4'-diacetoxyphenyl)-piperidine oxalate N-ethyl-3-(3',4'-dihydroxyphenyl)-piperidine hydrobromide, N-propyl-3-(3',4'-dihydroxyphenyl)-piperidine hydrobromide, N-benzyl-3-(3',4'-dihydroxyphenyl)-piperidine oxalate,N-benzyl-3-(3',4'-diacetoxyphenyl)-piperidine oxalate, N-(β-phenethyl)-3-(3',4'-dihydroxyphenyl)-piperidine fumarate, N-propyl-3-(3',4'-diacetoxyphenyl)-piperidine oxalate, N-isopropyl-3-(3',4'-dihydroxyphenyl)-piperidine hydrobromide and N-allyl-3-(3',4'-dihydroxyphenyl-piperidine hydrobromide.

The dopaminergic compositions are useful for the treatment of the symptoms of Parkinson disease, for the treatment of post-encephalitic parkinson syndromes, parkinson syndromes of arteriosclerous origin or toxic etiology.

The novel hypotensive compositions of the invention are comprised of an effective amount of a compound selected from the group consisting of N-benzyl-3-(3',4'-diacetoxyphenyl)-piperidine and N-(β-phenethyl)-3-(3',4'-dihydroxyphenyl)-piperidine and their non-toxic, pharmaceutically acceptable acid addition salts and an inert pharmaceutical carrier.

The novel method of treating the symptoms of Parkinson disease comprises administering to humans an effective amount of at least one compound of formula I and their non-toxic, pharmaceutically acceptable acid addition salts. The compounds may be administered orally, rectally or parenterally and the usual dose is 0.2 to 20 mg/kg.

The method of inducing hypotensive activity in warmblooded animals, including humans, comprises administering orally, rectally, or parenterally an effective amount of a compound selected from the group consisting of N-benzyl-3-(3',4'-diacetoxyphenyl)-piperidine and N-(β-phenethyl)-3-(3',4'-dihydroxyphenyl)-piperidine and their non-toxic, pharmaceutically acceptable acid addition salts. The usual effective dose is 0.2 to 20 mg/kg.

The compounds of formula II and be prepared by reacting 3-(3',4'-dimethoxyphenyl)-piperidine with an halide of the formula R-Hal' wherein Hal' is chlorine, bromine, iodine. When R is methyl, the compound of formula II may also be prepared by condensing formic aldehyde with 3-(3',4'-dimethoxyphenyl)-piperidine followed immediately by reduction with sodium cyano borohydride in acetonitrile in an acid media.

When R is alkyl of 2 to 5 carbon atoms, the compounds of formula II may be prepared by reacting 3-(3',4'-dimethoxyphenyl)-piperidine with an acid chloride of the formula $$R'-\overset{O}{\underset{\|}{C}}-Cl$$

wherein R' is alkyl of 1 to 4 carbon atoms to obtain a compound of the formula

[Structure of compound with CH₃O groups on phenyl, piperidine ring with N-C(=O)-R' substituent]

which is then reduced with lithium aluminum hydride in tetrahydrofuran.

The compounds of formula II wherein R is benzyl, may be prepared as described in copending, commonly assigned U.S. application Ser. No. 686,076 filed on even date herewith wherein 3,4-dimethoxy-bromo benzene is reacted with magnesium in an anhydrous ether to obtain $$\text{CH}_3\text{O}-\text{C}_6\text{H}_3(\text{OCH}_3)-\text{MgBr} \quad \text{III}$$

reacting the latter with N-benzyl-3-piperidone to obtain the compound of the formula

IV

[Structure: 3,4-dimethoxyphenyl-piperidine with N-benzyl and 3-OH]

dehydrating the latter with a strong acid to obtain a compound of the formula

V

[Structure: 3,4-dimethoxyphenyl-tetrahydropyridine with N-benzyl, dotted line indicating double bond]

wherein the dotted line indicates a double bond in the 2,3 or 3,4 position of the piperidine group and hydrogenating the latter in the presence of a hydrogenation catalyst such as palladium or palladium hydroxide in the presence of a lower alkyl acetate such as ethyl acetate to obtain a compound of formula II wherein R is benzyl.

The novel intermediates of the invention are 3-(3',4'-dimethoxypheny)-piperidines substituted on the nitrogen atom with propionyl, ethyl, propyl, allyl, isopropyl or β-phenethyl.

In the following examples there are described several preferred embodiments to illustrate the invention. However, it should be understood that the invention is not intended to be limited to the specific embodiments.

EXAMPLE 1

N-methyl-3-(3',4'-dihydroxyphenyl)-piperidine hydrobromide

STEP A:

N-benzyl-3-(3',4'-dimethoxyphenyl)-3-hydroxy-piperidine

A few drops of a solution of 75 g of 1-bromo-3,4-dimethoxy-benzene in 110 ml of tetrahydrofuran and an iodine crystal were added to 8.25 g of magnesium in 40 ml of tetrahydrofuran and the mixture was slighly heated. The rest of the solution of the above brominated compound was added at reflux which was maintained for an hour after which the solution was cooled to 20° C which contained the magnesium derivative of 1-bromo-3,4-dimethoxy-benzene.

A solution of 20 g of N-benzyl-3-piperidone in 100 ml of tetrahydrofuran was slowly added with cooling to a 150 ml of the preceding solution and the mixture was stirred at 20° C for 1 hour and then at 50° C for 2 hours.

The mixture was cooled and 250 ml of an aqueous solution saturated with ammonium chloride was slowly added. The mixture was extracted with ethyl acetate and the extracts were dried and evaporated to dryness. The residue was taken up in ethyl acetate and the solution was extracted with 2N hydrochloric acid. The acid extracts were made alkaline with sodium hydroxide and were extracted with ethyl acetate. The extracts were dried and evaporated to dryness and the residue was chromatographed over silica gel. Elution with an 85-10-5 cyclohexane-chloroform-triethylamine yielded 27.8 g of N-benzyl-3-(3',4'-dimethoxyphenyl)-3-hydroxy-piperidine.

STEP B:
N-benzyl-3-(3',4'-dimethoxyphenyl)-1,2,5,6-(and 1,4,5,6)-tetrahydropyridine A mixture of 2 g of N-benzyl-3(3',4'-dimethoxyphenyl)-3-hydroxy-piperidine and 20 ml of 2N hydrochloric acid was refluxed for 2 hours and was poured over ice. The mixture was made alkaline with sodium hydroxide and was extracted with methylene chloride. The extracts were dried and evaporated to dryness to obtain 1.76 g of a mixture of $\Delta^{2,3}$ and $\Delta^{3,4}$ isomers of N-benzyl-3-(3',4'-dimethoxyphenyl)-tetrahydropyridine. Chromatography of the product over silica gel and elution with an 85-10-5 cyclohexane-chloroform-triethylamine mixture yielded 0.66 g of the $\Delta^{3,4}$-isomer and 0.92 g of the $\Delta^{2,3}$-isomer.

STEP C: 3-(3',4'-dimethoxyphenyl)-piperidine

A mixture of 900 mg of 10% palladized activated carbon in 36 ml of ethanol was under a hydrogen atmosphere and 1.8 g of the $\Delta^{2,3}$ and $\Delta^{3,4}$ isomers of Step B were added thereto. The hydrogenation was continued until hydrogen adsorption ceased and the mixture was filtered to remove the catalyst. The filtrate was evaporated to dryness to obtain 1.1 g of 3-(3',4'-dimethoxyphenyl)-piperidine.

STEP D:
N-methyl-3-(3',4'-dimethoxyphenyl)-piperidine hydrochloride

A mixture of 2.85 g of 3-(3',4'-dimethoxyphenyl)-piperidine, 50 ml of acetonitrile and 7.15 ml of 30% formic aldehyde was stirred at 20° C for 10 minutes and then 1.33 g of sodium cyanoborohydride followed by 0.72 ml of acetic acid were added thereto. The mixture was stirred at 20° C for an hour and was then diluted with 100 ml of sodium hydroxide. The mixture was extracted with ethyl acetate and the extracts were dried and evaporated to dryness. The residue was dissolved in 40 ml of ethyl acetate and an ethyl acetate solution saturated with hydrochloric acid was slowly added thereto until crystallization and the mixture was then iced and vacuum filtered. The product was dried to obtain 3.02 g of N-methyl-3-(3',4'-dimethoxyphenyl)-piperidine hydrochloride melting at 211° C.

STEP E:
N-methyl-3-(3',4'-dihydroxyphenyl)-piperidine hydrobromide

A mixture of 8 g of the product of Step D in 40 ml of 66% hydrobromic acid was refluxed for an hour and then distilled to dryness under reduced pressure. The residue was dissolved in hot ethanol and the solution was cooled and vacuum filtered to obtain 2.49 g of N-methyl-3-(3',4'-dihydroxyphenyl)-piperidine hydrobromide as crystals melting at 190° C.

Analysis: $C_{12}H_{18}BrNO_2$: Calculated: %C: 50.01; %H: 6.30; %Br: 27.73; %N: 4.86; Found: C: 49.9; H: 6.3; Br: 27.4; N: 4.7.

EXAMPLE 2

N-methyl-3-(3',4'-diacetoxyphenyl)-piperidine oxalate 8.6 g of sodium acetate were added to a mixture of 7.55 g of N-methyl-3-(3',4'-dihydroxyphenyl)-piperidine hydrobromide and 95 ml of acetic acid anhydride cooled to 15° C and the mixture was stirred for 2 hours and then filtered. The filtrate was evaporated to dryness under reduced pressure and the residue was dissolved in 30 ml of ethanol. A solution of 3.2 g of oxalic acid in 30 ml of ethanol was added thereto and crystallization was effected. The mixture was vacuum filtered and the recovered crystals were crystallized from ethanol to obtain 1.2 g of N-methyl-3-(3',4'-diacetoxyphenyl)-piperidine oxalate melting at 171° C.

Analysis: $C_{18}H_{23}NO_8$: Calculated: %C: 56.7; %H: 6.08; %N: 3.67; Found: C: 56.4; H: 6.3; N: 3.5.

EXAMPLE 3

N-ethyl-3-(3',4'-dihydroxyphenyl)-piperidine hydrobromide

STEP A:
N-acetyl-3-(3',4'-dimethoxyphenyl)-piperidine

A mixture of 8 g of 3-(3',4'-dimethoxyphenyl)-piperidine, 80 ml of benzene and 3.6 ml of acetic acid anhydride was stirred at 20° C for an hour and was then diluted with 100 ml of water. 500 ml of an aqueous solution saturated with sodium bicarbonate were added thereto and the mixture was stirred for an hour and then was decanted. The aqueous phase was re-extracted with ethyl acetate and the organic phases were washed with water, dried and evaporated to dryness. The residue was chromatographed over silica gel and was eluted with a 6-3-1 cyclohexane-chloroform-triethylamine mixture to obtain 6.75 g of N-acetyl-3-(3',4'-dimethoxyphenyl)-piperidine.

STEP B: N-ethyl-3-(3',4'-dimethoxyphenyl)-piperidine

A solution of 680 mg of N-acetyl-3-(3',4'-dimethoxyphenyl)-piperidine in 10 ml of tetrahydrofouran was slowly added with stirring at 20° C to 200 mg of lithium aluminum hydride in 10 ml of tetrahydrofuran and the mixture was stirred for an hour and then cooled to 5° C. 10 ml of ethyl acetate were slowly added thereto and the mixture was poured into water and filtered. The aqueous phase was recovered by decanting and was extracted again with ethyl acetate. The combined organic phases were washed with water, dried and evaporated to dryness to obtain 600 mg of N-ethyl-3-(3',4'-dimethoxyphenyl)-piperidine melting at about 50° C.

STEP C: N-ethyl-3-(3',4'-dihydroxyphenyl)-piperidine hydrobromide

A mixture of 5.9 g of N-ethyl-3-(3',4'-dimethoxyphenyl)-piperidine and 30 ml of 66% hydrobromic acid was refluxed for an hour and was then evaporated to dryness under reduced pressure. The residue was crystallized from ethanol to obtain 5.9 g of N-ethyl-3-(3',4'-dihydroxyphenyl)-piperidine hydrobromide melting at 207° C.

Analysis: $C_{13}H_{20}BrNO_2$: Calculated: %C: 51.67; %H: 6.67; %Br: 26.44; %N: 4.63; Found: C: 51.4; H: 6.9; Br: 26.7; N: 4.7.

EXAMPLE 4

N-propyl-3-(3',4'-dihydroxyphenyl)-piperidine hydrobromide

STEP A:

N-propyl-3-(3',4'-dimethoxyphenyl)-piperidine 2 g of silver oxide and then 2 ml of propyl iodide were added to a solution of 4 g of 3-(3',4'-dimethoxyphenyl)-piperidine in 20 ml of chloroform and the mixture was stirred for 8 hours at 20° C under an inert atmosphere. Another 1 g of silver oxide and 1 ml of propyl iodide were added and the mixture was stirred for 15 hours. The mixture was filtered and the filtrate was evaporated to dryness. The residue was chromatographed over silica gel and eluted with a 6-3-1 cyclohexane-chloroform-triethylamine mixture to obtain 3.2 g of N-propyl-3-(3',4'-dimethoxyphenyl)-piperidine.

STEP B:

N-propyl-3-(3',4'-dihydroxyphenyl)-piperidine hydrobromide

A mixture of 4 g of N-propyl-3-(3',4'-dimethoxyphenyl)-piperidine and 40 ml of 66% hydrobromic acid acid was refluxed for an hour and was then evaporated to dryness. The residue was crystallized from isopropanol to obtain 4.4 g of N-propyl-3-(3',4'-dihydroxyphenyl)-piperidine hydrobromide melting at 211° C.

Analysis: $C_{14}H_{22}BrNO_2$: Calculated: %C: 53.17; %H: 7.01; Br: 25.27; %N: 4.43; Found: C: 53.2; H: 7.0; Br: 25.1; N: 4.3.

N-propyl-3-(3',4'-dimethoxyphenyl)-piperidine may also be obtained as follows

STEP A:

N-propionyl-3-(3',4'-dimethoxyphenyl)-piperidine 260 mg of sodium carbonate were added under a nitrogen atmosphere to a mixture of 500 mg of 3-(3',4'-dimethoxyphenyl)-piperidine in 5 ml of tetrahydrofuran and while cooling the mixture on an ice bath, 0.21 ml of propionyl chloride was added dropwise over 5 minutes. After the temperature rose to room temperature, the mixture was stirred for 1½ hours and was then poured into 10 volumes of ice and water. The mixture was extracted with methylene chloride and the extracts were washed with water, dried over magnesium sulfate and evaporated to dryness under reduced pressure. The 460 mg of residue was chromatography over silica gel and was eluted with a 6-3-1 cyclohexane-chloroform-triethylamine mixture. The product was crystallized to get 270 mg of amorphous N-propionyl-3-(3',4'-dimethoxyphenyl)-piperidine.

STEP B:

N-propyl-3-(3',4'-dimethoxyphenyl)-piperidine

A solution of 622 mg of N-propionyl-3-(3',4'-dimethoxyphenyl)-piperidine in 10 ml of anhydrous tetrahydrofuran was added dropwise over 15 minutes to a mixture of 170 mg of lithium aluminum hydride in 10 ml of tetrahydrofuran and the mixture was stirred for an hour at room temperature and was then iced. A 50—50 water-tetrahydrofuran mixture was added dropwise and the mixture was extracted with ethyl acetate. The organic extracts were washed with water, dried over magnesium sulfate and evaporated to dryness to obtain 543 mg of product. The product was chromatographed over silica gel and was eluted with a 6-3-1 cyclohexane-chloroform-triethylamine mixture to obtain 423 mg of N-propyl-3-(3',4'-dimethoxyphenyl)-piperidine in the form of a pale yellow oil.

EXAMPLE 5

N-benzyl-3-(3',4'-dihydroxyphenyl)-piperidine oxalate

STEP A:

N-benzyl-3-(3',4'-dimethoxyphenyl)-piperidine 5 g of the mixture of $\Delta^{2,3}$ and $\Delta^{3,4}$ isomers of Step B of Example 1 were dissolved in 200 ml of ethyl acetate and 2.5 g of 10% palladized activated carbon and hydrogen were added until hydrogen absorption ceased. The mixture was filtered to remove catalyst and the filtrate was evaporated to dryness. The residue was chromatographed over silica gel and was eluted with an 85-10-5 cyclohexane-chloroform-triethylamine mixture to obtain 2.7 g of N-benzyl-3-(3',4'-dimethoxyphenyl)-piperidine.

STEP B:

N-benzyl-3-(3',4'-dihydroxyphenyl)-piperidine oxalate

A mixture of 5.25 g of the product of Step A in 53 ml of 66% hydrobromic acid was refluxed for an hour and was then distilled to dryness under reduced pressure. The residue was taken up in water and methylene chloride was added thereto. The mixture was made alkaline with sodium bicarbonate and the organic phase was recovered by decanting, was dried and evaporated to dryness. The residue was dissolved in 50 ml of isopropanol and a solution of 1 g of oxalic acid in 30 ml of isopropanol was added. The mixture was refluxed and after crystallization, was cooled and vacuum filtered. The recovered crystals were dried to obtain 4.9 g of N-benzyl-3-(3',4'-dihydroxyphenyl)-piperidine oxalate melting at 208° C.

Analysis: $C_{19}H_{22}NO_4$: Calculated: %C: 69.49; %H: 6.75; %N: 4.27; Found: C: 69.4; H: 6.6; N: 4.1.

EXAMPLE 6

N-benzyl-3-(3',4'-diacetoxyphenyl)-piperidine oxalate 9.8 g of anhydrous sodium acetate were added to a mixture of 9.8 g of N-benzyl-3-(3',4'-dihydroxyphenyl)-piperidine oxalate and 120 ml of acetic acid anhydride and the mixture was stirred for 3 hours at 20° C and was filtered. The filter was washed with ethanol and the filtrate was evaporated to dryness under reduced pressure. The residue was taken up in water and ethyl acetate and the solution was made alkaline with an aqueous solution saturated with sodium bicarbonate. The organic phase was decanted, dried and evaporated to dryness. The residue was dissolved in 50 ml of isopropanol and a solution of 4 g of oxalic acid in 30 ml of isopropanol was added thereto. The mixture was refluxed until dissolution occurred and after cooling to 20° C, the mixture was vacuum filtered to obtain 13.5 g of N-benzyl-3-(3',4'-diacetoxyphenyl)-piperidine oxalate melting at 145° C.

Analysis: $C_{24}H_{27}NO_8$: Calculated: %C: 63.01; %H: 5.95; %N: 3.06; Found: C: 63.0; H: 6.0; N: 3.0.

EXAMPLE 7

N-(β-phenylethyl)-3-(3',4'-dihydroxyphenyl)-piperidine fumarate

STEP A:
N-(β-phenylethyl)-3-(3',4'-dimethoxyphenyl)-piperidine 500 mg of silver oxide were added to a mixture of 1 g of 3-(3',4'-dimethoxyphenyl)-piperidine in 5 ml of chloroform and then 0.7 ml of phenethyl bromide was added thereto dropwise. The mixture was stirred for 6 hours at room temperature and then 250 mg of silver oxide and 0.35 ml of phenethyl bromide were added thereto. The mixture was stirred at room temperature for 16 hours and was filtered to remove insolubles. The filtrate was evaporated to dryness under reduced pressure and the residue was chromatographed over silica gel. Elution with a 6-3-1 cyclohexane-chloroform-triethylamine mixture yielded 1.045 g of amorphous N-(β-phenylethyl)-3-(3',4'-dimethoxyphenyl)-piperidine.

STEP B:
N-(β-phenylethyl)-3-(3',4'-dihydroxyphenyl)-piperidine fumarate

A mixture of 3.3 g of N-(β-phenylethyl)-3-(3',4'-dimethoxyphenyl)-piperidine and 33 ml of 66% hydrobromic acid was refluxed for an hour and was then distilled to dryness under reduced pressure. The residue was taken up in a water-methylene chloride mixture and was made alkaline with an aqueous solution saturated with sodium bicarbonate. The organic phase was decanted and the aqueous phase was extracted with methylene chloride. The combined organic phases were washed with water, dried over magnesium sulfate and distilled to dryness under reduced pressure to obtain 2.67 g of N-(β-phenylethyl)-3-(3',4'-dihydroxyphenyl)-piperidine.

A solution of 1.67 g of said compound in 20 ml of methanol was reacted with a solution of 320 mg of fumaric acid in methanol and crystallization was induced. The mixture was iced and vacuum filtered and the crystals were washed with methanol and dried under reduced pressure to obtain 1.58g of N-(β-phenylethyl)-3-(3',4'-dihydroxyphenyl)-piperidine fumarate in the form of beige crystals melting at 178° C.

Analysis: $C_{21}H_{25}NO_4$: Calculated: %C: 70.96; %H: 7.09; %N: 3.91; Found: C: 71.1; H: 7.1; N: 3.9.

EXAMPLE 8

N-propyl-3-(3',4'-diacetoxyphenyl)-piperidine oxalate

STEP A: N-propyl-3-(3',4'-diacetoxyphenyl)-piperidine

A suspension of 3.5 g of N-propyl-3-(3',4'-dihydroxyphenyl)-piperidine hydrobromide in 40 ml of acetic acid anhydride was stirred with 3.5 g of sodium acetate for 3 hours at 20° C and the mixture was then filtered. The filtrate was evaporated to dryness and the residue was taken up in a water-ethyl acetate mixture. The mixture was made alkaline with sodium bicarbonate addition and the organic phase was recovered by decanting. The organic phase was washed with water, dried and evaporated to dryness to obtain 3.3 g of N-propyl-3-(3',4'-diacetoxyphenyl)-piperidine.

STEP B: N-propyl-3-(3',4'-diacetoxyphenyl)-piperidine oxalate

A solution of 1.4 g of oxalic acid in 20 ml of isopropanol was added to a solution of 3.5 g of the product of Step A in 20 ml of isopropanol and the mixture was held at 0° C for a few hours and was then vacuum filtered. The crystals were washed with isopropanol and were crystallized from isopropanol to obtain 4.2 g of N-propyl-3-(3',4'-diacetoxyphenyl)-piperidine oxalate melting at 150° C.

Analysis: $C_{20}H_{27}NO_8$: Calculated: %C: 58.67; %H: 6.65; %N: 3.42; Found: C: 58.8; H: 6.8; N: 3.3.

EXAMPLE 9

N-isopropyl-3-(3',4'-dihydroxyphenyl)-piperidine hydrobromide

STEP A:
N-isopropyl-3-(3',4'-dimethoxyphenyl)-piperidine 2.5 g of silver oxide were added to a solution of 5 g of 3-(3',4'-dimethoxyphenyl)-piperidine in 25 ml of acetone and then 2.5 ml of isopropyl iodide were added dropwise. The mixture was stirred at 20° C for 24 hours and was filtered. The filtrate was evaporated to dryness and the residue was chromatographed over silica gel. Elution with a 6-3-1 cyclohexane-chloroform-triethylamine mixture yielded 4.8 g of N-isopropyl-3-(3',4'-dimethoxyphenyl)-piperidine.

STEP B:
N-isopropyl-3-(3',4'-dihydroxyphenyl)-piperidine hydrobromide

A solution of 4.8 g of N-isopropyl-3-(3',4'-dimethoxyphenyl)-piperidine in 48 ml of 66% hydrobromic acid was refluxed for an hour and was evaporated to dryness. The residue was crystallized from isopropanol and then acetone to obtain 4.2 g of N-isopropyl-3-(3',4'-dihydroxyphenyl)-piperidine hydrobromide melting at 182° C.

Analysis: $C_{14}H_{22}BrNO_2$: Calculated: %C: 53.17; %H: 7.01; %N: 4.43; %Br: 25.27; Found: C: 53.0; H: 7.1; N: 4.3; Br: 24.9.

EXAMPLE 10

N-allyl-3-(3',4'-dihydroxyphenyl)-piperidine hydrobromide

STEP A: N-allyl-3-(3',4'-dimethoxyphenyl)-piperidine 2.8 g of silver oxide were added to a solution of 5.6 g of 3-(3',4'-dimethoxyphenyl)-piperidine in 28 ml of acetone and then 2.3 ml of allyl bromide were added dropwise thereto with slow cooling. The mixture was stirred at 20° C for 30 minutes and was then filtered. The filtrate was evaporated to dryness and the residue was chromatographed over silica gel. Elution with a 6-3-1 cyclohexane-chloroform-triethylamine mixture yielded 5.55 g of N-allyl-3-(3',4'-dimethoxyphenyl)-piperidine.

STEP B: N-allyl-3-(3',4'-dihydroxyphenyl)-piperidine hydrobromide

A solution of 5.55 g of N-allyl-3-(3',4'-dimethoxyphenyl)-piperidine in 55 ml of 66% hydrobromic acid was refluxed for an hour and was evaporated to dryness. The residue was crystallized from isopropanol and then acetonitrile to obtain 3.27 g of N-allyl-3-(3',4'-dihydroxyphenyl)-piperidine hydrobromide melting at 235° C.

Analysis: $C_{14}H_{20}BrNO_2$: Calculated: %C: 53.51; %H: 6.42; % Br: 25.43; %N: 4.46; Found: C: 53.1; H: 6.4; Br: 25.3; N: 4.3.

EXAMPLE 11

Tablets were prepared with 50 mg of N-methyl-3-(3',4'-dihydroxyphenyl)-piperidine hydrobromide or N-ethyl-3-(3',4'-dihydroxyphenyl)-piperidine hydrobromide or N-benzyl-3-(3',4'-dihydroxyphenyl)-piperidine oxalate and sufficient excipient consisting of lactose, starch, talc and magnesium stearate to make a final tablet of 200 mg.

PHARMACOLOGICAL DATA

A. Antagonism against reserpinic rigidity

The antagonism of the tested products against reserpinic rigidity was determined in rats using the procedure of Jurna I: Arch. Pharmak. Exp. Path., Vol. 260 (1968), p. 80–88 and the electromyogram (EMG) provoked by a dorsiflexion of the foot was determined with electrodes placed on the muscles of the anterior loge of the hind foot of the animal. A dose of 10 mg/Kg of reserpine was administered intraveinously and 30 minutes later when the muscle hypertonicity was maximal, the tested product was administered intraveinously at a dose of 10 or 20 mg/Kg. The electromyogram responses were determined before and after the administration of the tested compound and were compared for their intensity and duration. The inhibition observed on the electromyogram showed antagonism provoked by the tested product against the reserpine induced rigidity and the results were expressed in an increasing number of + as a function of the dose in mg/Kg. The results are reported in Table I.

TABLE I

| Compound of Example | Antagonism against reserpine, dose in mg/kg |
|---|---|
| 1 | ++ 20 |
| 2 | ++ 20 |
| 3 | + 20 |
| 4 | + 20 |
| 5 | +++ 20 |
| 6 | +++ 20 |
| 7 | ++ 10 |
| 8 | ++ 20 |
| 9 | + 20 |

The results of Table I show that the tested products were very active, especially the compounds of Examples 5, 6 and 7 at a dose of 20 mg/kg.

B. Behavior after unilateral injury of nigrostriatal bundle

Among the animals having undergone a unilateral lesion of nigrostriatal bundle, the substances, having a dopaminergic activity induce a rotating behavior. The animals were male rats weighing about 250 g and female mice weighing about 22 g. The lesion was effected in test (a) in the right striatum of the male rats with a 2 mA anodic current for a duration of 30 seconds /Anden et al, Acta. Pharmacol. Toxicol., Vol. 24 (1966), p. 263–274/. The tested compounds were administered intraperitoneally to groups of 6 animals and they were individually placed in a rotometer which counted the number of rotations of each animal in two directions. Each test was continued for 1½ hours.

In test (b) with the male rats, lesion was effected in the substantia nigra of each rat with 6-hydroxydopamine monohydrochloride at a dose of 20 μg per 4 μl of physiological serum containing 0.2 mg/ml of ascorbic acid by the method of Ungerstedt /Acta. physiol. scand., 1971 a, supp 367, p. 69–93/and the same conditions as in (a) were used.

In test (c) with female mice, a lesion of the striatum was effected with a hypodermic needle with a diameter of 0.5 mm by aspiration under vacuum for 5 seconds with the method of Lotti /Life Science, Vol. 10 (1971) I, p. 781–789/. The tested compounds were intraperitoneally administered and the mice were observed for an hour to determine the number of mice showing rotation movements.

The compounds of Examples 3 and 8 showed ipsilateral rotations at a dose of 25 mg/kg in test (a) and contralateral rotations at a dose of 25 mg/kg in test (b). The compound of Example 7 showed ipsilateral rotations at a dose of 10 mg/kg in test (a) and contralateral rotations at a dose of 10 mg/kg in test (b). The compounds of Examples 4,5 and 6 showed ipsilateral rotation at a dose of 25 mg/kg in test (a) and at a dose of 100 mg/kg in test (c) and the compounds of Examples 4,5,6 and 10 showed contralateral rotations at a dose of 25 mg/kg in test (b).

C. Hypotensive activity

The hypotensive activity was determined on male rats of the Sprague-Dawley S.P.F. strain weighing about 300 g and anesthesized with nembutal at an intraveinous dose of 50 mg/kg. The test product was administered intraveinously into the jugular vein and the carotid blood pressure was measured before and after the administration of the tested compound. The variation in the arterial pressure after the administration of the tested compound as compared to the initial arterial pressure as well as the time necessary for the pressure to return to the initial value were determined. Under the test conditions, the product of Example 6 exerted a hypotension of 20 to 30% for more than one hour at a dose of 10 mg/kg. The compound of Example 7 exercises an hypotension of 30% for more than an hour at a dose of 1 mg/kg and this hypotension was 5 to 10% for 10 minutes at a dose of 0.1 mg/kg.

D. Acute toxicity

The 50% lethal dose ($LD_{50}$) was determined for the products after intraperitoneal administration to mice and the mortality was determined 48 hours after the administration of the tested product. The $LD_{50}$ for the products is reported in Table II.

TABLE II

| Compound of Example | $LD_{50}$ in mg/kg |
|---|---|
| 1 | 150 |
| 2 | 150 |
| 3 | 150 |
| 4 | 150 |
| 5 | 150 |
| 6 | 300 |
| 7 | 150 |
| 8 | 250 |
| 9 | 150 |
| 10 | 150 |

Various modifications of the products and methods of the invention may be made without departing from the spirit or scope thereof and it is to be understood that the invention is to be limited only as defined in the appended claims.

We claim:

1. A compound selected from the group consisting of a compound of the formula

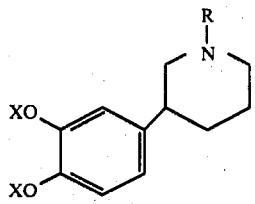

wherein X is selected from the group consisting of hydrogen and acyl of an alkanoic acid of 2 to 6 carbon atoms and R is selected from the group consisting of alkyl of 1 to 5 carbon atoms, alkenyl of 2 to 5 carbon atoms and phenylalkyl of 1 to 3 alkyl carbon atoms and their non-toxic, pharmaceutically acceptable acid addition salts.

2. A compound of claim 1 wherein R is selected from the group consisting of methyl, ethyl, propyl, isopropyl, allyl, benzyl and phenethyl.

3. A compound of claim 2 wherein X is selected from the group consisting of hydrogen, acetyl and pivaloyl.

4. A compound of claim 1 which is selected from the group consisting of N-methyl-3-(3',4'-dihydroxyphenyl)-piperidine and its hydrobromide.

5. A compound of claim 1 which is selected from the group consisting of N-ethyl-3-(3',4'-dihydroxyphenyl)-piperidine and its hydrobromide.

6. A compound of claim 1 which is selected from the group consisting of N-propyl-3-(3',4'-dihydroxyphenyl)-piperidine and its hydrobromide.

7. A compound of claim 1 which is selected from the group consisting of N-isopropyl-3-(3',4'-dihydroxyphenyl)-piperidine and its hydrobromide.

8. A compound of claim 1 which is selected from the group consisting of N-allyl-3-(3',4'-dihydroxyphenyl)-piperidine and its hydrobromide.

9. A compound of claim 1 which is selected from the group consisting of N-methyl-3-(3',4'-diacetoxyphenyl)-piperidine and its oxalate.

10. A compound of claim 1 which is selected from the group consisting of N-benzyl-3-(3',4'-diacetoxyphenyl)-piperidine and its oxalate.

11. A compound of claim 1 which is selected from the group consisting of N-propyl-3-(3',4'-diacetoxyphenyl)-piperidine and its oxalate.

12. A compound of claim 1 which is selected from the group consisting of N-benzyl-3-(3',4'-dihydroxyphenyl)-piperidine and its oxalate.

13. A compound of claim 1 which is selected from the group consisting of N-($\beta$-phenethyl)-3-(3',4'-dihydroxyphenyl)-piperidine and its fumarate.

14. A dopaminergic composition comprising an dopaminergically effective amount of at least one compound of claim 1 and an inert pharmaceutical carrier.

15. An hypotensive composition comprising an hypotensively effective amount of at least one compound selected from the group consisting of N-benzyl-3-(3',4'-diacetoxyphenyl)-piperidine and N-($\beta$-phenethyl)-3-(3',4'-dihydroxyphenyl)-piperidine and their non-toxic, pharmaceutically acceptable acid addition salts.

16. A method of treating the symptoms of Parkinson disease comprising administering to humans an effective amount of at least one compound of claim 1.

17. The method of claim 16 wherein R is selected from the group consisting of methyl, ethyl, propyl, isopropyl, allyl, benzyl and phenethyl and X is selected from the group consisting of hydrogen, acetyl and pivaloyl.

18. A method of inducing hypotensive activity in warm-blooded animals comprising administering to warm-blooded animals an hypotensively effective amount of at least one compound selected from the group consisting of N-benzyl-3-(3',4'-diacetoxyphenyl)-piperidine and N-($\beta$-phenethyl)-3-(3',4'-dihydroxyphenyl)-piperidine and their non-toxic, pharmaceutically acceptable acid addition salts.

* * * * *